US006812217B2

(12) United States Patent
Hendriks (10) Patent No.: US 6,812,217 B2
(45) Date of Patent: Nov. 2, 2004

(54) MEDICAL DEVICE AND METHODS OF USE

(75) Inventor: Marc Hendriks, Brunssum (NL)

(73) Assignee: Medtronic, Inc., Minneapolis, MN (US)

( * ) Notice: Subject to any disclaimer, the term of this patent is extended or adjusted under 35 U.S.C. 154(b) by 114 days.

(21) Appl. No.: 09/727,461

(22) Filed: Dec. 4, 2000

(65) Prior Publication Data
US 2003/0091609 A1 May 15, 2003

(51) Int. Cl.[7] ............................................. A61K 48/00
(52) U.S. Cl. ........................ 514/44; 623/66; 435/320.1; 424/450
(58) Field of Search .................. 623/66; 435/320.1, 435/455, 458; 514/44; 424/450, 93.2; 604/20

(56) References Cited

U.S. PATENT DOCUMENTS

| | | | |
|---|---|---|---|
| 4,944,659 A | | 7/1990 | Labbe et al. |
| 5,077,056 A | | 12/1991 | Bally et al. |
| 5,521,291 A | * | 5/1996 | Curiel ..................... 530/391.7 |
| 5,674,722 A | | 10/1997 | Mulligan et al. |
| 5,714,577 A | * | 2/1998 | Montelaro .................. 530/324 |
| 5,833,651 A | | 11/1998 | Donovan et al. |
| 5,877,302 A | | 3/1999 | Hanson et al. |
| 5,993,850 A | | 11/1999 | Sankaram et al. |
| 6,143,037 A | * | 11/2000 | Goldstein et al. ............. 623/66 |
| 6,206,914 B1 | * | 3/2001 | Soykan ...................... 623/1.42 |
| 6,219,577 B1 | * | 4/2001 | Brown, III .................... 604/20 |
| 6,228,845 B1 | * | 5/2001 | Donovan ...................... 514/44 |
| 6,273,875 B1 | * | 8/2001 | Siman et al. ................ 604/264 |
| 6,409,716 B1 | * | 6/2002 | Sahatjian .................... 604/509 |
| 6,451,044 B1 | * | 9/2002 | Naghavi ...................... 607/96 |
| 2003/0031780 A1 | * | 2/2003 | Chudzik et al. ............. 427/2.1 |
| 2003/0078226 A1 | * | 4/2003 | German ....................... 514/44 |

FOREIGN PATENT DOCUMENTS

| | | |
|---|---|---|
| WO | WO96/28841 | 9/1996 |
| WO | WO/96/34417 | 10/1996 |

OTHER PUBLICATIONS

Ausubel, R.M., ed., *Current Protocols in Moleclular Biology*, (1994).
Boman et al., "Antimicrobial Peptides," *Ciba Foundation Symposium*, John Wiley and Sons, Chicester (1994).
Dichek et al., *Mol. Biol. Med.*, 8, 257–266 (1991).
*Homo sapiens* defensin, alpha 5, Paneth cell–specific (DEFA5), mRNA; GenBank Accession No. NM_021010 (Available on or before Nov. 29, 2000).
*Homo sapiens* mRNA for liver–expressed antimicrobial peptide (leap–1 gene); Genbank Accession No. AJ277280 (Available on or before Nov. 29, 2000).
*Homo sapiens* beta–defensin 3 mRNA, complete cds; Genbank Accession No. AF295370 (Available on or before Nov. 29, 2000).
*Homo sapiens* mRNA for beta–defensin–3; Genbank Accession No. AJ237673 (Available on or before Nov. 29, 2000).
*Homo sapiens* beta defensin–3 mRNA, complete cds; GenBank Accession No. AF217245 (Available on or before Nov. 29, 2000).
*Homo sapiens* cathelicidin antimicrobial peptide (CAMP), mRNA; GenBank Accession No. NM_004345 (Available on or before Nov. 29, 2000).
*Homo sapiens* beta defensin 2 (HBD2) gene, complete cds; GenBank Accession No. AF071216 (Available on or before Nov. 29, 2000).
*Homo sapiens* beta–defensin–1 gene, exon 2 and complete cds; GenBank Accession No. U50931 (Available on or before Nov. 29, 2000).
*Homo sapiens* beta–defensin 2 (DEFB2) gene, complete cds; GenBank Accession No. AF040153 (Available on or before Nov. 29, 2000).
*H.sapiens* mRNA for skin–antimicrobial–peptide 1 (SAP1); GenBank Accession No. Z71389 (Available on or before Nov. 29, 2000).
Human beta–defensin–1 mRNA, complete cds; GenBank Accession No. U73945 (Available on or before Nov. 29, 2000).
*H.sapiens* defensin 5 gene, complete cds; GenBank Accession No. M97925 (Available on or before Nov. 29, 2000).
*H.sapiens* mRNA for FALL–39 peptide antibiotic; GenBank Accession No. Z38026 (Available on or before Nov. 29, 2000).
Krijgsveld et al., *J. Biol. Chem.*, 275, 20374–20381 (2000).
Sambrook et al., *Molecular Cloning: A Laboratory Manual.*, Cold Spring Harbor Laboratory Press (1989).
Smela et al., *Science*, 268, 1735–1738 (1995).
Turner et al., *Antimicrob. Agents Chemother.*, 42, 2206–2214 (1998).

* cited by examiner

Primary Examiner—Dave T Nguyen
(74) Attorney, Agent, or Firm—Paul H. McDowall; Girma Wolde-Michael; Thomas F. Woods (57) ABSTRACT

The present invention provides a medical device that includes a carrier and a polynucleotide, where the carrier has a surface that includes a polymer with which the polynucleotide is associated. In another aspect, the present invention provides a medical device that includes a carrier and a cell that expresses an antimicrobial peptide, where the carrier has a surface that includes a polymer with which the cell is associated. The present invention further provides methods of making and using medical devices that include a carrier and a polynucleotide or a cell.

23 Claims, 1 Drawing Sheet

FIG. 1

MEDICAL DEVICE AND METHODS OF USE

FIELD OF THE INVENTION

The present invention relates to medical devices (e.g., implantable pulse generators) that include a polymer and a polynucleotide. Preferably, the medical device can be used to prevent or treat medical device-associated infections. In some aspects of the present invention, the medical devices carry a polynucleotide that encodes an antimicrobial peptide and inhibits the growth of pathogens. In other aspects of the present invention, the medical devices carry eukaryotic cells (e.g., endothelial cells) that express an antimicrobial peptide and inhibit the growth of pathogens.

BACKGROUND

The insertion of implants has become a widely accepted and often life-saving procedure. The past few years have seen a dramatic increase in the variety and numbers of medical devices. It is estimated that currently world-wide there are some 6,000 distinct types or generic groups of medical devices, and some 750,000 or more brands and models, ranging from very simple devices to very complex systems. A study in 1989 estimated that world-wide approximately 1,000,000 implants are performed annually; the number of additionally used catheters for diagnostic and therapeutic means exceeds this number considerably.

Infection is the most feared, if not the most serious complication of the numerous devices and materials inserted. Treatment of such infections is difficult and most often infection is irreversible, requiring in many cases complete removal of the catheter or implant. Technological refinements in materials and design and increasing surgical experience generally lowers the incidence of infectious complications; however, infection remains a constant cause of morbidity and mortality.

The impact and clinical importance of implant-related infections may be more appreciated considering several factors. One important factor is the millions of patients in whom prostheses of one sort or another are present. Another important factor is the severity of illness that results from device-related infections. In most instances, infection involving a totally implanted device results in function-loss and the need for surgical removal in order to achieve a cure. Depending on the device type, e.g., with prosthetic heart valves or vascular grafts, mortality is high following infection. A third factor is the economic consequences that are measured in the costs of making the diagnosis and in treating a device-related infection. It is estimated that the costs of treating an infected joint prosthesis exceed four- to sixfold the costs of the original prosthetic joint replacement.

Approaches to reduce device-related infections initially were focused on improvements of the surgical technique, including modification of the operating room area and the use of prophylactic antibiotics at the time of surgery. Despite the introduction of these meticulous aseptic measures the occurrence of device-related infections could not be completely eliminated.

An alternative approach is to focus on the implant itself, and consequently on modification of the device to enhance infection-resistance by providing surfaces on the device that promote appropriate integration of the surrounding tissue(s) with the device surface. The underlying concept is that encouraging rapid colonization and integration of the device surface with tissue cells protects the implant surface from bacterial colonization.

A considerable amount of attention and study has been directed toward preventing colonization of bacterial and fungal organisms on the surfaces of orthopedic implants by the use of antimicrobial agents, such as antibiotics, bound to the surface of the materials employed in such devices. The objective of such attempts has been to produce a sufficient bacteriostatic or bactericidal action to prevent colonization. Practice of the prior art coating methods results in an orthopedic implant or medical device wherein the effectiveness of the coating can diminish over time. After insertion of the medical device or orthopedic implant, the antibiotics can leach from the surface of the device into the surrounding environment. Moreover, bacterial pathogens have become increasingly resistant to commonly used antibiotics. In some cases, there are no remaining first-line options for therapy. A recently published trend analysis on bacterial pathogens isolated from blood in England and Wales from 1990 to 1998 showed an upward trend in total numbers of reports of bacteraemia. The five most cited organisms accounted for over 60% of reports each year. There was a substantial increase in the proportion of reports of *Staphylococcus aureus* resistant to methicillin, *Streptococcus pneumoniae* resistance to penicillin and erythromycin, and *Enterococcus faecalis* and *Enterococcus faecium* resistance to vancomycin.

Antimicrobial peptides are a type of antibiotic. The first antimicrobial peptides were identified in 1939 by Dubos who demonstrated that 'an unidentified soil bacillus' produced antibacterial compounds that could prevent pneumococcal infections in mice (Boman et al., "Antimicrobial Peptides," Ciba Foundation Symposium, John Wiley and Sons, Chicester (1994)). In the 1960s, a bee venom toxin and a peptide in frog skin were claimed to be antibacterial. Since then, antimicrobial peptides have been isolated from insects (cecropins from the moth *Hyalophora cecropia* and *Drosophila melanogaster*, insect defensins from the fleshflies *Phormia terranovae* and *Sacrophaga peregrina*), from the skin of the African clawed frog *Xenopus laevis* (magainins), from the horse shoe crab (tachyplesins), and mammalian granulocytes (defensins), macrophages (murine microbicidal proteins), and platelets (thrombocidins). Their widespread distribution is remarkable and makes it highly likely that these components play an important protective role as a first line of defense against infections. Although antimicrobial peptides vary considerably in length, almost all of them are of cationic nature.

In humans, numerous antimicrobial peptides have been isolated and characterized from multiple sources, including neutrophils (also referred to in the art as polymorphonuclear leukocytes), T cells, bronchoalveolar lavage, platelets, plasma, wound fluid, and various organs. Furthermore, over the past few years a range of antimicrobial peptides have been found in epithelial tissue of airways, urogenital tissue, skin, and intestine. These findings suggest that host defense by means of antimicrobial peptides might be more general than ever was assumed initially.

Antimicrobial peptides are able to kill a wide variety of gram-positive and gram-negative bacteria. At least three sequential events are required for target cell lysis: membrane binding; permeabilization; and finally damaging of DNA. It is believed that after binding to the cell membrane, the antimicrobial peptides form voltage-dependent channels in the lipid bilayers of the cell membrane. The amphiphatic nature of antimicrobial peptides makes them soluble in aqueous media and promotes their ability to insert in membranes. The net positive charge on antimicrobial peptides favors interactions with negatively charged lipid head groups, and provides an initial driving force for insertion of an antimicrobial peptide into a membrane. Moreover, this mechanism of action is one which bacteria have difficulty evading by developing resistance.

TABLE 1

Documents cited herein.

U.S. Patents:

| U.S. Pat. No. | Inventor(s) | Issue Date |
| --- | --- | --- |
| 4,944,659 | Labbe et al. | Jul. 31, 1990 |
| 5,077,056 | Bally et al. | Dec. 31, 1991 |
| 5,674,722 | Mulligan et al. | Oct. 7, 1997 |
| 5,877,302, | Hanson | Mar. 2, 1999 |
| 5,993,850 | Sankaram et al. | Nov. 30, 1999 |

International Patent Applications:

| Application No. | Inventor(s)/Applicant(s) |
| --- | --- |
| WO 96/28841 | Smela et al. |
| WO 96/34417 | Smela et al. |

Other documents:

Ausubel, R.M., ed. Current Protocols in Molecular Biology (1994)
Boman et al., "Antimicrobial Peptides," Ciba Foundation Symposium, John Wiley and Sons, Chicester (1994)
Dichek et al., Mol.Biol.Med., 8 257–266 (1991)

Genbank Accession Nos:

NM_021010,
AJ277280,
AF295370,
AJ237673,
AF217245,
NM_004345,
AF071216,
U50931,
AF040153,
Z71389,
U73945,
M97925,
Z38026.

Krijgsveld et al., J.Biol.Chem., 275, 20374–20381 (2000)
Sambrook et al, Molecular Cloning: A Laboratory Manual., Cold Spring Harbor Laboratory Press (1989)
Smela et al. Science, 268, 1735–1738 (1995)
Turner et al., Antimicrob.AgentsChemother., 42, 2206–2214 (1998)

All documents listed in Table 1 hereinabove are hereby incorporated by reference herein in their respective entireties. As those of ordinary skill in the art will appreciate readily upon reading the Summary of the Invention, Detailed Description of the Preferred Embodiments, and claims set forth below, many of the devices and methods disclosed in the documents of Table 1 may be modified advantageously by using the teachings of the present invention.

SUMMARY OF THE INVENTION

The present invention has certain objects. That is, various embodiments of the present invention provide solutions to one or more problems existing in the prior art with respect to preventing infections associated with implantable medical devices. Those problems include the continued prevalence of infections associated with medical devices, and the ineffectiveness of traditional antibiotics to prevent infection by resistant strains of microorganisms. Various embodiments of the present invention have the object of solving at least one of the foregoing problems.

In comparison with known medical devices, various embodiments of the present invention provide one or more of the following advantages: (a) inhibiting the growth of pathogenic microorganisms by exposure of the microorganisms to antimicrobial peptides; (b) providing a polynucleotide encoding an antimicrobial peptide to a cell present in a patient such that the cell expresses the antimicrobial peptide; (c) providing a cell that expresses an antimicrobial peptide; and (d) making an antimicrobial peptide available at the site of implantation of a medical device and thereby decreasing the likelihood of a medical device associated infection.

Some embodiments of the invention include one or more of the following features: (a) a carrier having a surface that includes a polymer and a polynucleotide associated with at least a portion of the polymer, where the polynucleotide is not present in a cell; and (b) a carrier having a surface that includes a polymer and a cell associated with at least a portion of the polymer, where the cell expresses an antimicrobial peptide.

Definitions

The terms "medical device," "carrier," and "implantable pulse generator" are described in greater detail herein.

As used herein, the term "porous polymer" refers to a polymer that has pores distributed throughout, and is capable of absorbing liquids.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. An "introduced polynucleotide" is a polynucleotide that has been introduced to a cell, for instance by ex vivo gene transfer. A polynucleotide can be, for example, a portion of a vector, such as an expression vector, or a fragment.

The phrase "not present in a cell" means the polynucleotide is not present in a eukaryotic or a prokaryotic cell, and is not present in a viral particle.

As used herein, the phrase "associated with" in the context of polynucleotides or cells refers to how they are combined with a carrier polymer. The polynucleotides or cells can be, for instance, incorporated into a polymeric coating or film on the carrier, coated on top of a polymeric coating or film on the carrier, or present under a polymeric coating or film on the carrier. The polynucleotides or cells can also be incorporated into microscopic containment vehicles which are incorporated into a polymeric coating or film on the carrier, coated on top of a polymeric coating or film on the carrier, or present under a polymeric coating or film on the carrier.

As used herein, the term "film" refers to a sheet material.

As used herein, the phrase "natural porous polymer" refers to a polymer that is present in or produced by nature, i.e., it is not artificial or man-made.

As used herein, the phrase "synthetic porous polymer" refers to a polymer that is artificial or man-made, i.e., it is not present in or produced by nature.

"Coding region" and "coding sequence" are used interchangeably and refer to a nucleotide region that encodes a polypeptide and, when placed under the control of appropriate regulatory sequences expresses the encoded polypeptide. The boundaries of a coding region are generally determined by a translation start codon at its 5' end and a translation stop codon at its 3' end. A regulatory sequence is a nucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

"Peptide" and "polypeptide" are used interchangeably herein to refer to a polymer of amino acids and does not refer to a specific length of a polymer of amino acids. Thus, for example, the terms oligopeptide, protein, and enzyme are included within the definition of peptide. This term also includes post-expression modifications of the peptide, for example, glycosylations, acetylations, phosphorylations, and the like. The term "antimicrobial peptide" is described in detail herein.

The term "condensed" as used herein describes a polynucleotide that has been compacted to isolated spheres or toroids so that the interaction of the DNA with the solvent is minimal.

As used herein, the phrase "linked to a receptor ligand" refers to attachment of a receptor ligand to the surface of an encapsulated or condensed polynucleotide. The attachment can be by a covalent bond, hydrogen bonding, or Van der Waals forces.

Unless otherwise specified, "a," "an," "the," and "at least one" are used interchangeably throughout the specification and mean one or more than one.

DETAILED DESCRIPTION OF THE PREFERRED EMBODIMENTS

Medical Devices

The present invention provides medical devices that include a polymer and a polynucleotide associated with the polymer. The polynucleotide is not present in a cell. Preferably, the medical devices are useful for the prevention or treatment of medical device-associated infections. In some aspects of the invention, the medical devices include a carrier and a polynucleotide. Preferably, the polynucleotide includes a coding region that encodes an antimicrobial peptide. In other aspects, the medical devices include a carrier and a cell that expresses an antimicrobial peptide.

A variety of carriers can be used in the medical devices of the present invention, including, for example, stents, vascular grafts, stent grafts, synthetic patches, infusion sleeves, medical electrical leads and electrodes, indwelling catheters, heart valves, annuloplasty rings, ear tubes, cerebrospinal fluid shunts, implantable drug pumps, and implantable pulse generators (IPGs) and the electrical leads associated with IPGs. Examples of IPGs include pacemakers, implantable cardioverter defibrillators, implantable defibrillators, and neurostimulators. Any of these devices can be used as carriers for the polynucleotides or cells of the invention. The following description focuses on IPGs, although it applies equally to other medical devices.

Figure 1:
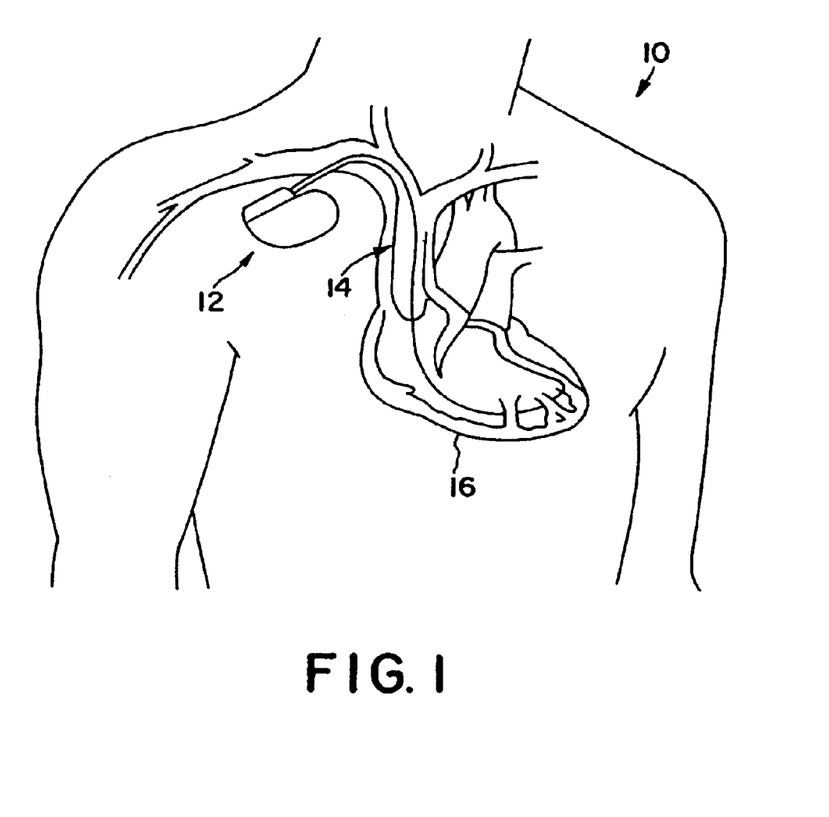
FIG. 1 shows an implantable pulse generator (IPG) 12 implanted in a patient 10.

FIG. 1 shows a preferred aspect of the invention where the IPG 12 is inserted into a pocket that is formed in the patient 10, for instance in the left pectoralis major area, a traditional pacemaker implant site. The IPG has a surface that contacts the tissue that makes up the wall of the pocket into which the IPG has been implanted. The IPG can be coated with a natural or synthetic polymeric coating or film for holding the polynucleotides or cells in place. Polymeric coatings and films are described in greater detail herein.

Whether the carrier is an IPG or other medical device, the polynucleotides or cells are associated with the carrier polymer. The medical devices of this invention preferably include a first polymer composition in which the polynucleotides or cells are present. The first polymer composition of this invention can be prepared from a homopolymer, a copolymer (i.e., a polymer of two or more different monomers), or a composition (e.g., a blend) with one or more polymers or copolymers, for example. The composition preferably forms a viscoelastic, tear-resistant, biocompatible polymer. The term "viscoelastic" refers to the prescribed "memory" characteristics of a molecule that allow the molecule to respond to stress as if the molecule was a combination of elastic solids and viscous fluids. The term "tear resistent" indicates that when the polymer is exposed to expansion stress, the material does not substantially tear. Tearing refers to the propagation of a nick or cut in the material while under stress. The term "biocompatible" is used herein to refer to a material that does not have toxic or injurious effects on biological systems.

Preferably, the first polymer composition decreases or does not exacerbate irritation to the tissue surrounding the pocket into which the IPG is inserted. The first polymer composition is preferably non-inflammatory and nonthrombogenic when applied alone or alternatively when used with anti-thrombogenic agents such as heparin, and the like, or with anti-inflammatory agents such as cyclosporins, and the like. The first polymer composition is also preferably a biostable or a bioabsorbable polymer depending on the desired rate of release or the desired degree of polymer stability.

The first polymer compositions of this invention can include one or more synthetic or natural polymers. Suitable polymers include those that are compatible with the polynucleotides or the cells. Preferably, the first polymer is a porous polymer. In one aspect of the invention, the porous polymer is a film on at least a portion of the structure. In another aspect, the porous polymer is an integral portion of the structure. Preferably, the porous polymer is biocompatible, and sufficiently tear-resistant, non-inflammatory, and nonthrombogenic. Preferably, the porous polymer is biodegradable.

Preferably, the porous polymer is a natural porous polymer or a synthetic porous polymer. Examples of natural porous polymers include gelatin, fibrin, collagen, elastin, hyaluronic acid, chondroitin sulfate, dermatan sulfate, heparin sulfate, heparin, cellulose, chitin, chitosan, mixtures or copolymers thereof, or a wide variety of others typically disclosed as being useful in implantable medical devices. Examples of synthetic porous polymers include silicone, polyurethane, polysulfone, polyethylene, polypropylene, polyamide, polyester, polycarboxylic acids, polyvinylpyrrolidone (PVP), maleic anhydride polymers, polyamides, polyvinyl alcohols (PVA), polyethylene oxides, polyacrylic acid polymers, polytetrafluoroethylene, polyhydroxyethylmethacrylic acid (pHEMA), polyaminopropylmethacrylamide (pAPMA), polyacrylamido-2-methylpropanesulfonic acid (pAMPS), polyacrylamide, polyacrylic acid, mixtures or copolymers thereof, or a wide variety of others typically disclosed as being useful in implantable medical devices. Additional examples of synthetic porous polymers include biodegradable synthetic porous polymers, such as polyglycolic acid, polylactic acid, polydiaxonone, poly(,-caprolactone), polyanhydrides, poly(Ǝ-hydroxybutyrate), poly(ortho esters), poly(amino acids), polyiminocarbonates, and mixtures or copolymers thereof. In materials which do not include pores in their usual structural configurations, pores between one micrometer in diameter or as large as 1000 micrometers in diameter can be introduced by conventional means such as by introducing a solvent soluble particulate material into the desired structure and dissolving the particulate material with a solvent. However, no particular pore size is critical to this invention. Those skilled in the art will recognize that the methods for forming the first polymer composition can be modified to include other polymers, as contemplated in this invention, without undue experimentation.

In one aspect of the present invention, the porous polymer is made of a polymer other than fibrin and has fibrin incorporated within the pores. Typically, and preferably, such a porous polymer is in the form of a sheet material of a synthetic polymer that is biostable. Such synthetic biostable polymers include silicone, polyurethane, polysulfone, cellulose, polyethylene, polypropylene, polyamide, polyester, polytetrafluoroethylene, and combinations thereof.

If the porous polymer is in the form of a porous sheet or film, it can be made by a variety of methods. These methods can include, for example, forming the films using a solid particulate material that can be substantially removed after the film is formed, thereby forming pores. By using a solid particulate material during film formation, the size of the pores can, to some extent, be controlled by the size of the solid particulate material being used. The particulate material can range from less than about 1 micrometer in diameter to about 1000 micrometers, preferably about 1 micrometer to about 100 micrometers, more preferably about 25 micrometers to about 60 micrometers. For uniformity of pores, the particulate material can be screened through successively finer mesh sieves, e.g., through 100, 170, 270, 325, 400, and 500 mesh analytical grade stainless steel mesh sieves, to produce a desired range of particle sizes.

In one method according to the present invention, a porous polyurethane sheet material can be made by dissolving a polyether urethane in an organic solvent such as N-methyl-2-pyrrolidone; mixing into the resulting polyurethane solution a crystalline, particulate material like a salt or sugar that is not soluble in the solvent; casting the solution with particulate material into a thin film; and then applying a second solvent, such as water, to dissolve and remove the particulate material, thereby leaving a porous sheet. A portion of the particulate material may remain within the film. As a result, it is preferred that the solid particulate material be biocompatible.

Drugs, for instance, but not limited to anticoagulants, such as heparin, warfarin, aspirin, hirudin, and tissue plasminogen activator, or anti-inflammatory agents, such as dexamethasone, beclamethasone, cyclosporin, and superoxide dismutase, can be incorporated into the IPG prior to implantation in an amount effective to prevent or limit thrombosis or inflammation. A drug immersion procedure can be used to incorporate the drug. A solution of the drug can alternatively be added at the time that polynucleotides or the cells are added to the IPG. The drug can also be incorporated into the polymer matrix before it has completely polymerized. For example, powdered drug can be dusted onto the IPG during the polymerization process.

The shape of the polymer film or coating can be modified based on the methods used to cover the IPG. It can be spray coated onto the IPG or a film can be molded over the IPG. The first polymer composition of this invention can cover at least a portion of the IPG.

The IPG can also be positioned within a mold and the compounds forming the first polymer composition incorporated into the mold. The first polymer composition forming a sheet or sleeve can be prepared in an extended shape and then compressed or dehydrated into a final shape to fit over the IPG.

Polynucleotides or cells can be added to the IPG by mixing the monomer solution of the first polymer composition with polynucleotides or cells or by directly applying the polynucleotides or cells to the polymerized composition. In one aspect, polynucleotides or cells are added to the IPG at the time of formation of the first polymer composition.

Alternatively, the polynucleotides or cells can be added to the polymer coated IPG either at the time of device manufacture, or by the physician prior to device implantation. Where the first polymer composition is capable of dehydration and rehydration, the IPG can be supplied in a sterile, dehydrated form and polynucleotides or cells can be added to the IPG by rehydration of the first polymer composition positioned on the IPG by immersing, wicking, or spraying a liquid containing the polynucleotides or cells onto the IPG prior to IPG implantation. An example of such a liquid for addition of polynucleotides is, for instance, 10 mM Tris-HCl and 1 mM EDTA, about pH 7.4 to about pH 8.0 (TE buffer), and the like. An example of such a liquid for addition of cells is, for instance, a balanced salt solution, including HBSS or a tissue culture media, and the like. The liquid used to deliver polynucleotides or cells to the first polymer coating should support the stability of the polynucleotides or cells and should include pH buffered solutions, in a form that is biocompatible and preferably nonimmunogenic. Optionally, the liquid can include stabilizers such as albumin, glycerol, or the like. Optionally, the polynucleotides can be present in association with compounds that aid delivery of the polynucleotide to a cell. Such compounds include liposomes and condensing agents, and are described in detail herein. Where the polynucleotides or cells are incorporated into a polymer solution for spray application or air pump applications, the polymer should be of sufficiently low viscosity to facilitate the application of the solution to the IPG.

In another aspect of the IPGs of this invention, a second polymer composition can be added over the first polymer composition following, or at the time of, adding the polynucleotides or cells. Preferably, the second polymer composition is biodegradable and the second polymer composition coats at least a portion of the first polymer composition and polynucleotides. For example, after the polynucleotides or cells are added to an IPG having a first polymer composition coated thereon, the IPG can be sprayed with or immersed in a solution to form a coating of a biodegradable polymer such as collagen, gelatin, polylactic acid, or methylcellulose, with or without a coagulation inhibitory or anti-inflammatory compound. Advantageously, the second covering of polymer provides even greater sustained release capabilities. Suitable polymers for use in the second polymer composition include, but are not limited to, those listed above for the first polymer composition, and combinations thereof, or a wide variety of others typically disclosed as being useful in IPGs.

The polynucleotides or cells can also be included within a microscopic containment vehicle that can be stimulated to release the polynucleotides or the antimicrobial peptides expressed by the cells. This microscopic containment vehicle can be coated onto the delivery device directly or into or onto a polymer coating or film. The polynucleotides or cells are enclosed within such a vehicle. Upon stimulation of the containment vehicle, the polynucleotides or the antimicrobial peptides expressed by the cells are released from the containment vehicle. Stimulation of the containment vehicles can be accomplished using a variety of techniques known to the art.

Examples of microscopic containment vehicles include, but are not limited to, those described in International Patent Application Nos. WO 96/28841 (Ohman) and WO 96/34417 (Smela et al.) and Smela et al., Science, 268, 1735–1738 (1995), which disclose micromachined structures and microactuators. In one example, such micromachined structures include conducting bilayers made of a layer of polymer and a layer of gold that are used as hinges to connect rigid plates to each other and to a silicon substrate. The bending of the hinges is electrically controlled and reversible, allowing precise three-dimensional positioning of the plates. The use of differential adhesion allows the structures to be released from the silicon substrate. Thus, complex shapes can be formed, such as cubes, of micrometer size that could be used to contain polynucleotides or cells in association with a medical device such as an IPG, until they are needed for therapeutic or preventative treatment.

Microscopic containment vehicles can also include micropumps, reservoirs, with piezoelectric valves. The body of the pump and reservoir can be made of a polymeric material while the valves contain a piezoelectric material, which allows opening and closing of the valves and pumping movement by electrical stimulation. The reservoirs contain the polynucleotides or cells. Upon stimulation of the piezoelectric material, the valve is opened to release the polynucleotides or the antimicrobial peptides expressed by the cells. Implantable piezoelectric pumps are known (see, for example, U.S. Pat. No. 4,944,659 (Labbe et al.)) and can be modified by one of skill in the art to form containment vehicles for the present invention.

In another aspect, the present invention also provides methods for local delivery to a patient of a polynucleotide or local delivery to a patient of a cell encoding an antimicrobial peptide. The methods include providing a medical device that includes a carrier that has a polymer associated with it, and a polynucleotide associated with at least a portion of the polymer. Alternatively, the methods include providing a medical device that includes a carrier and a polymer, and a cell associated with at least a portion of the polymer. The cell expresses an antimicrobial peptide.

The present invention further provides methods for making a medical device for local delivery of a polynucleotide or local delivery of a cell encoding an antimicrobial peptide. The IPGs of this invention can be provided in a sterile, dehydrated form, in a hydrated form with polynucleotides or cells or as a first polymer covered IPG supplied with the necessary materials to facilitate adding the polynucleotides or cells and further coating or covering of the IPG as needed. Therefore, this invention also relates to a kit that includes an IPG with a first polymer composition, buffers suitable for rehydrating the IPG and adding the polynucleotides or cells and a container to facilitate sterile addition of the polynucleotide to the IPG. Optionally, the kit can include further coatings or coverings to be applied over the first polymer composition. In a preferred aspect, the kit includes: an IPG that includes a surface that contacts the tissue of a patient, and a first polymer composition covering at least a portion of the surface of the IPG; a polynucleotide-adding or cell-adding composition to be applied to the IPG; and a container to house the IPG and the composition during application of the polynucleotide-adding or cell-adding composition.

Polynucleotides

The polynucleotides of the present invention can be associated with the medical devices of the present invention, or can be introduced to a cell that is associated with the medical devices of the present invention. Such cells are described herein in the section entitled "Cells expressing an antimicrobial peptide." The polynucleotides include a coding region that encodes a peptide, preferably an antimicrobial peptide. Antimicrobial peptides are also referred to in the art as peptide antibiotics. An antimicrobial peptide is a peptide that will inhibit the growth of, or kill, pathogens, i.e., microorganisms that cause disease. Typically an antimicrobial peptide is between about 5 amino acids to about 150 amino acids in length.

The antimicrobial peptides encoded by the polynucleotides that are associated with the medical devices of the present invention aid in the prevention or treatment of medical device-associated infections. The polynucleotides are released from the carrier and are taken up by cells adjacent to the carrier in the patient, for instance, cells present in the tissue that makes up the wall of the pocket into which the carrier has been implanted. Preferably, the polynucleotides are released from the carrier over a period of time (i.e., there is a sustained release of the polynucleotides), preferably during the first 14 days after implantation, more preferably during the first 7 days after implantation.

The infections can be caused by pathogens including viruses, fungi, or bacteria. The types of bacteria that can cause medical device-associated infections include gram-positive and gram-negative bacteria, including, for example, *Staphylococcus aureus, Staphylococcus epidermidis*, Streptococcus spp., and Enterococcus spp.

A polynucleotide encoding an antimicrobial peptide can be obtained from, for instance, insect, bacterial, amphibian, marine, mammal, and plant sources. Preferably, the polynucleotide is from a human. Whether the peptide encoded by a polynucleotide is an antimicrobial peptide can be tested using methods known to the art. For instance, Turner et al. (*Antimicrob. Agents Chemother.*, 42, 2206–2214 (1998)) disclose radial diffusion assays, broth microdilution assays, and colony counting assays to measure the antimicrobial properties of a peptide. The antimicrobial properties of a peptide can also be measured by evaluating membrane permeabilization, for instance, the membrane permeabilization of the inner and outer membranes of, for instance, *E. coli* (Turner et al., *Antimicrob. Agents Chemother.*, 42, 2206–2214 (1998)). Other methods for testing the antimicrobial properties of a peptide are available at, for instance, Steinberg et al. (In: Methods in Molecular Biology, Vol. 78: Antibacterial peptide protocols, Shafer (ed.), Humana Press, Totowa, New Jersey, pp. 169–186 (1997)). Without intending to be limiting, examples of polynucleotides encoding antimicrobial peptides include thrombocidins (see Krijgsveld et al., *J. Biol. Chem.*, 275, 20374–20381 (2000), and the coding sequences disclosed at the following GenBank Accession numbers; NM_021010, AJ277280, AF295370, AJ237673, AF217245, NM_004345, AF071216, U50931, AF040153, Z71389, U73945, M97925, Z38026. Optionally, a polynucleotide encoding an antimicrobial peptide can further include a coding region that encodes a signal peptide. Nucleotide sequences encoding many signal peptides are well known to the art and can be linked to a coding region so that the nucleotides encoding a signal peptide and the nucleotides that include a coding region are contiguous and in the same reading frame.

The coding region encoding the antimicrobial peptide is typically inserted in a vector. A vector is a replicating polynucleotide, such as a plasmid vector, viral vector, cosmid vector, or artificial chromosome vector, to which another polynucleotide may be attached so as to bring about the replication of the attached polynucleotide. A vector can be linear or circular. Preferably, the vector is a plasmid. A vector provides for the expression of the antimicrobial peptide encoded by the coding region. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994). Typically, a vector is capable of replication in a bacterial host, for instance *E. coli*. Optionally, a vector is capable of replication in a eukaryotic cell. Preferably, a vector does not integrate into the genomic DNA present in a eukaryotic cell.

A vector optionally includes regulatory sequences operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the patient receiving the medical device.

Promoter sequences are known for eukaryotes. Operably linked to 25 to 30 bases upstream from the site where transcription is initiated. Often, another sequence found 70 to 80 bases upstream from the start of transcription is the CXCAAT region where X may be any nucleotide. Operably linked to the 3' end of most eukaryotic coding regions is an AATAAA sequence that may be a signal for addition of the poly A tail to the 3' end of mRNA that results from transcription of the coding sequence. These sequences can be suitably inserted into a vector. The promoter that is normally operably linked to a coding region encoding an antimicrobial peptide can also be used.

Transcription of a coding region encoding an antimicrobial peptide from vectors in the cell of a patient receiving a medical device of the present invention can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, and Hepatitis-B virus.

Transcription in a patient's cell of a coding region encoding an antimicrobial peptide can be increased by inserting an enhancer sequence into the vector. Enhancers are cis-acting elements of DNA, usually having about 10 to 300 nucleotides, that act on a promoter to increase its transcription. Enhancers are relatively orientation- and position-independent, having been found 5' and 3' to coding regions, within an intron as well as within the coding sequence itself. Many enhancer sequences are now known from mammalian genes (globin, elastase, albumin, alpha-fetoprotein, and insulin). Enhancers from eukaryotic cell viruses are also known and include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the coding region encoding an antimicrobial peptide, but is preferably located at a site 5' of the promoter.

A vector can optionally include a ribosome binding site (e.g., a Kozak site) and a start site (e.g., the codon ATG) to initiate translation of the transcribed message to produce the antimicrobial peptide. It can also include a termination sequence to end translation. A termination sequence is typically a codon for which there exists no corresponding aminoacetyl-tRNA, thus ending peptide synthesis. The vector can optionally further include a transcription termination sequence. Transcription termination sequences in vectors for eukaryotic cells typically include a polyadenylation signal 3' of the coding region.

The polynucleotides that are included as a part of the medical device can be present as naked DNA. For instance, the polynucleotides can be dissolved in solution, or precipitated by, for example, calcium phosphate. Alternatively, the polynucleotides can be enclosed. For example, the polynucleotides can be enclosed in a synthetic lipid bilayer vesicle, including, for instance, a liposome. Examples of liposomes include multivesicular liposomes, unilamelar liposomes multilamellar liposomes and plurilamellar liposomes. Liposome encapsulation can provide for the controlled release of polynucleotides present in the liposomes. Methods of producing liposomes that control the rate of release of an encapsulated material into an aqueous environment are known to the art (see, for instance, U.S. Pat. No. 5,993,850 (Sankaram et al.); and U.S. Pat. No. 5,077,056 (Bally et al.)).

The polynucleotides can be condensed. Condensed DNA is DNA that has been compacted to isolated spheres or toroids so that the interaction of the DNA with the solvent is minimal. DNA can be compacted to a condensed state by neutralizing its charge, e.g., by addition of a polycation, or otherwise reducing its interactions with solvent. However, the polycation can cause aggregation or precipitation of the DNA if a chaotropic agent is not employed to prevent it. Compaction therefore can be accomplished by judicious use of both the polycation (to condense the DNA) and (as needed) of a chaotropic agent (to prevent aggregation or precipitation). Methods for condensing DNA are known to the art, see, for instance, U.S. Pat. No. 5,877,302 (Hanson). Examples of polycations include, for instance, polylysine, Arg-Lys mixed polymers, polyarginine, polyornithine, histones, avidin, protamines, and polyethyleneimine.

Optionally, a polynucleotide that is encapsulated or condensed can be actively directed to selected cell types, preferably granulocytes, monocytes, macrophages, neutrophils, platelets, T-cells, B-cells, or fibroblasts. One method used to direct liposomes actively to selected target cells involves attachment of antibodies which bind specifically to an epitope on the surface of the target cell. Methods for raising antibodies against cells, cell membranes, or isolated cell surface antigens are known in the art. Another method used to direct liposomes actively to selected target cells involves attachment of receptor ligands to the surface of the encapsulated or condensed polynucleotides. Preferably, the receptor ligand is covalenty attached, for instance, by cross-linking the ligand to the surface of the encapsulated or condensed polynucleotide. Preferably, a receptor ligand is specifically bound by a receptor carried by the target cells. One class of receptor ligands of interest is carbohydrates, especially mono- and oligosaccharides. Suitable ligands include galactose, lactose, and mannose. For example, mannose can be used as a receptor ligand to target the polynucleotide to macrophages and monocytes, and mannose-6-phosphate can be used as a receptor ligand to target the polynucleotide to fibroblasts.

Cells Expressing an Antimicrobial Peptide

Cells suitable for use in the present invention include a wide variety of eukaryotic cells that express antimicrobial peptides. The cells (for example, a macrophage) can naturally express an antimicrobial peptide. Alternatively, the cells can be modified to include a polynucleotide described herein (see the section entitled "Polynucleotides") such that the cell expresses an antimicrobial peptide. A cell that naturally expresses an antimicrobial peptide (for example, a macrophage) can be modified to include a polynucleotide encoding an antimicrobial peptide. Preferably, the cells that are associated with a medical device are also able to secrete the antimicrobial peptides. Suitable cells for use in the present invention typically include inflammatory cells, including, for instance, macrophages. Other suitable cells are mesenchymal or mesodermal cells, including, but not limited to endothelial cells and fibroblasts, whether they are autologous or allogeneic, genetically engineered or not modified to include a polynucleotide encoding an antimicrobial peptide. Mixtures of such cells can also be used. Inflammatory cells are particularly suitable for use in the present invention because they naturally express antimicrobial peptides.

Preferably, the cells used are suitable to be modified to include a polynucleotide encoding an antimicrobial peptide, for instance by ex vivo gene transfer. Ex vivo gene transfer is a process by which cells are removed from a body, preferably the body of the patient that is to receive the IPG, and using well known techniques are genetically manipulated, usually through the introduction, e.g., by transfection, of polynucleotides into the cells in vitro. The modified cells are then returned to the body for therapeutic purposes. A polynucleotide that has been introduced to a cell, for instance by ex vivo gene transfer, is referred to as an introduced polynucleotide. Ex vivo gene transfer is an effective approach because the target cells to be used in the procedure can be manipulated as needed to optimize gene transfer efficiency and thus the effectiveness of the overall procedure. Typically, the ex vivo gene transfer uses cell types that can be readily retrieved from the body, cultured ex vivo, and then returned to the body. Such cells include blood and marrow cells, liver hepatocytes, skin fibroblasts, muscle myoblasts, vascular endothelial cells, and inflammatory cells.

There are a wide variety of methods that can be used to deliver polynucleotides to the eukaryotic cells if they are to be modified to express, preferably secrete, an antimicrobial peptide. These are well known to one of skill in the art. The desired polynucleotide can be inserted into an appropriate vector. There are a number of viruses, live or inactive, including recombinant viruses, that can also be used. A retrovirus can be genetically modified to deliver any of a variety of coding regions. Adenovirus has been used in a variety of experiments to deliver polynucleotides capable of directing and expressing a polypeptide in a cell.

Depending on the maximum genome size that a particular viral genome can accommodate or that can be associated with a virus particle, the virus delivering polynucleotide to the cell can include a polynucleotide encoding one or more polypeptides.

In one embodiment of the present invention, endothelial cells are obtained from a patient and grown in cell culture. During proliferation in cell culture, they are infected with a genetically engineered retrovirus which integrates the coding region encoding the antimicrobial peptide into the chromosomes of the infected cells. This can be accomplished, for example, according to the teachings of U.S. Pat. No. 5,674, 722 (Mulligan et al.) and Dichek et al., Mol. Biol. Med., 8, 257–266 (1991).

The cells can be coated directly on the carrier and covered by a polymer, incorporated into the polymer, or coated on top of a polymeric coating or film on the carrier. They can also be included within a microscopic containment vehicle that can be stimulated to release the antimicrobial peptide expressed by the cells. The microscopic containment vehicle can be coated on the carrier and covered by a polymer, incorporated into the polymer, or coated on top of a polymeric coating or film on the carrier. Preferably, the cells express the antimicrobial peptide over a period of time, preferably during the first 14 days after implantation, more preferably during the first 7 days after implantation.

The preceding specific embodiments are illustrative of the practice of the invention. It is to be understood, therefore, that other expedients known to those skilled in the art of disclosed herein, may be employed without departing from the invention or the scope of the appended claims. The present invention further includes within its scope methods of making and using the medical devices described hereinabove.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. An implantable medical device comprising;
   a housing having an exterior surface;
   a polymer film applied to the exterior surface of the implantable medical device housing; and
   a polynucleotide associated with at least a portion of the polymer whereby said polynucleotide encodes for antimicrobial peptide, thus providing for an antimicrobial effect after said polynucleotide is released from said polymer film and said polynucleotide is expressed in and the encoded antimicrobial peptide is delivered by the cells and tissues surrounding said medical device.

2. The medical device of claim 1 wherein the implantable medical device is an implantable pulse generator.

3. The medical device of claim 1 wherein the polymer is a porous polymer.

4. The medical device of claim 3 wherein the porous polymer is a natural porous polymer.

5. The medical device of claim 4 wherein the natural porous polymer is selected from the group consisting of collagen, gelatin, elastin, fibrin, hyaluronic acid, and a glycosaminoglycan.

6. The medical device of claim 3 wherein the porous polymer is a synthetic porous polymer.

7. The medical device of claim 6 wherein the synthetic porous polymer is a biodegradable synthetic porous polymer selected from the group consisting of polyglycolic acid, polylactic acid, polydiaxonone, poly(,-caprolactone), polyanhydrides, poly(∃-hydroxybutyrate), poly(ortho esters), poly(amino acids), polyiminocarbonates, and mixtures thereof.

8. The medical device of claim 1 wherein the polynucleotide is condensed.

9. The medical device of claim 8 wherein the condensed polynucleotide is linked to a receptor ligand.

10. The medical device of claim 1 wherein the polynucleotide is enclosed in a liposome.

11. The medical device of claim 10 wherein the enclosed polynucleotide is linked to a receptor ligand.

12. A method for reducing implantable medical device-related infections in a patient, the method comprising;
providing a medical device comprising a housing having a surface provided with a polymer film; and
providing a polynucleotide associated with at least a portion of the polymer; and wherein the polynucleotide is released from the medical device upon being implanted in a patient whereby said polynucleotide encodes for an antimicrobial peptide, thus providing an antimicrobial effect after said polynucleotide is expressed in and the encoded antimicrobial peptide is delivered by the cells and tissues surrounding said medical device.

13. The method of claim 12 wherein the carrier is an implantable pulse generator.

14. The method of claim 12 wherein the polymer is a porous polymer.

15. The method of claim 14 wherein the porous polymer is a natural porous polymer.

16. The method of claim 15 wherein the natural porous polymer is selected from the group consisting of collagen, gelatin, elastin, fibrin, hyaluronic acid, and a glycosaminoglycan.

17. The method of claim 14 wherein the porous polymer is a synthetic porous polymer.

18. The method of claim 17 wherein the synthetic porous polymer is a biodegradable synthetic porous polymer selected from the group consisting of polyglycolic acid, polylactic acid, polydiaxonone, poly(,-caprolactone), polyanhydrides, poly($\exists$-hydroxybutyrate), poly(ortho esters), poly(amino acids), polyiminocarbonates, and mixtures thereof.

19. The method of claim 12 wherein the polynucleotide is condensed.

20. The method of claim 10 wherein the condensed polynucleotide is linked to a receptor ligand.

21. The method of claim 12 wherein the polynucleotide is enclosed in a liposome.

22. The method of claim 21 wherein the enclosed polynucleotide is linked to a receptor ligand.

23. A method for reducing implantable medical device-related infections in a patient, the method comprising:
providing an implantable medical device comprising a housing having a surface provided with a polymer film;
providing a polynucleotide; and
contacting the polymer with the polynucleotide, whereby said polynucleotide encodes for an antimicrobial peptide thus providing for an antimicrobial effect after said polynucleotide is released from said polymer film and said polynucleotide is expressed in and the encoded antimicrobial peptide is delivered by the cells and tissues surrounding said medical device.

* * * * *

UNITED STATES PATENT AND TRADEMARK OFFICE
CERTIFICATE OF CORRECTION

PATENT NO.    : 6,812,217 B2
DATED         : November 2, 2004
INVENTOR(S)   : Marc Hendriks It is certified that error appears in the above-identified patent and that said Letters Patent is hereby corrected as shown below:

Column 10,
Lines 22-23, delete "peptide thus" and insert -- peptide, thus --.

Column 15,
Line 10, delete "patient whereby" and insert -- patient, whereby --.

Signed and Sealed this

Twenty-fourth Day of May, 2005

JON W. DUDAS
*Director of the United States Patent and Trademark Office*